United States Patent [19]

Ducoin et al.

[11] Patent Number: 5,267,981
[45] Date of Patent: Dec. 7, 1993

[54] HYGIENE AND TREATMENT DEVICE

[76] Inventors: Jacques Ducoin, 26, Rue des Remparts, FR-21140 Semur En Auxois; Claude Franceschi, 21, quai A. Le Gallo, FR-92100 Boulogne, both of France

[21] Appl. No.: 717,266

[22] Filed: Jun. 18, 1991

[30] Foreign Application Priority Data

Jun. 19, 1990 [FR] France ............................ 90 07624

[51] Int. Cl.$^5$ ............................................ A61M 31/00
[52] U.S. Cl. ....................................... 604/275; 604/85; 604/19; 433/89; 128/66
[58] Field of Search ..................... 604/82–85, 604/19, 48, 275, 289; 128/200.22, 200.23, 66; 433/88, 89, 120

[56] References Cited

U.S. PATENT DOCUMENTS

| | | | |
|---|---|---|---|
| 2,855,012 | 8/1944 | Reifsnyder | 433/89 |
| 3,164,153 | 1/1965 | Zorzi | 433/88 |
| 3,254,647 | 6/1966 | Vogel | 604/85 |
| 3,386,439 | 6/1968 | Harper | 604/84 |
| 4,390,017 | 6/1983 | Harrison | 604/275 |
| 4,564,005 | 1/1986 | Marchand et al. | 604/84 |
| 4,735,200 | 4/1988 | Westerman | 128/66 |
| 4,871,360 | 10/1989 | Theeuwes | 604/85 |
| 4,894,053 | 1/1990 | Reddick | 604/85 |
| 4,903,688 | 2/1990 | Bibby et al. | 128/66 |
| 4,911,704 | 3/1990 | Dixon | 604/83 |
| 4,973,307 | 11/1990 | Theeuwes | 604/85 |
| 5,095,893 | 3/1992 | Rawden, Jr. | 128/66 |

*Primary Examiner*—C. Fred Rosenbaum
*Assistant Examiner*—Chalin Smith
*Attorney, Agent, or Firm*—Eckert, Seamans, Cherin & Mellott

[57] ABSTRACT

A hygiene and treatment device wherein it comprises a pipe having a chamber at one of its ends, suitable for being put into communication with an endpiece connected to a supply of water under pressure, the other end of the pipe being curved and having a longitudinal slot. The invention is particularly suitable for anal and gynecological hygiene.

7 Claims, 2 Drawing Sheets

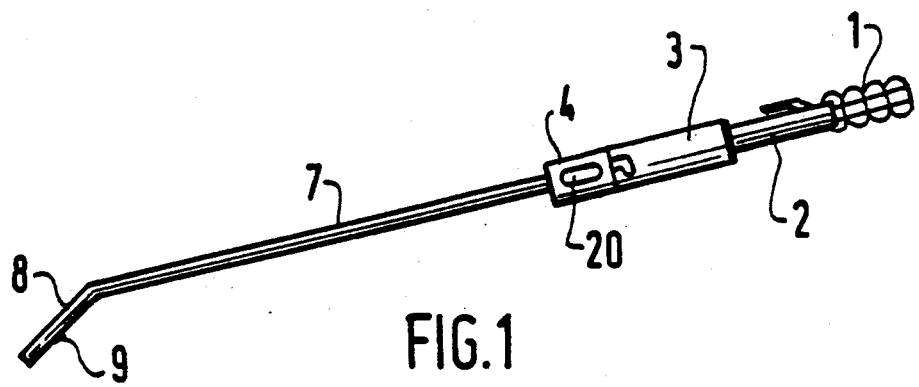
FIG.1
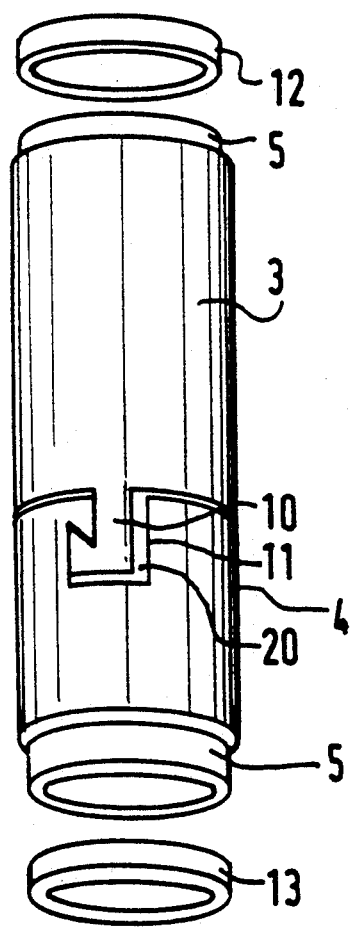
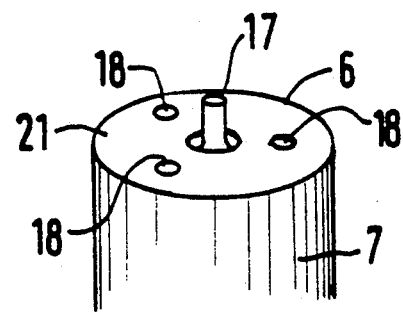
FIG.4
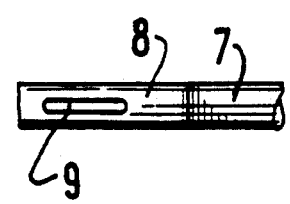
FIG.5
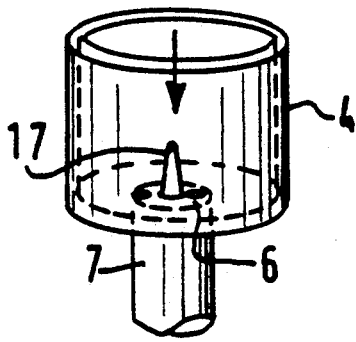
FIG.2

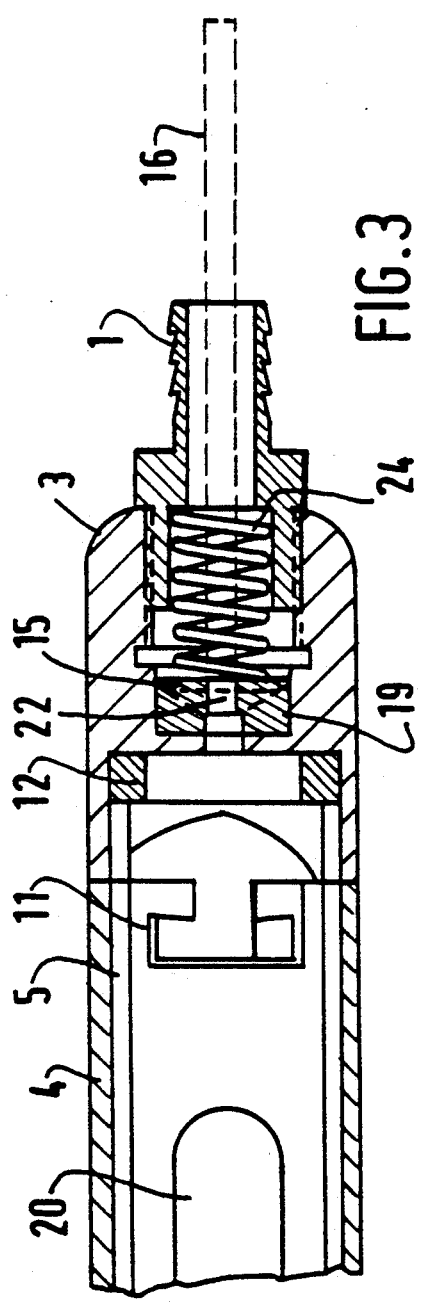
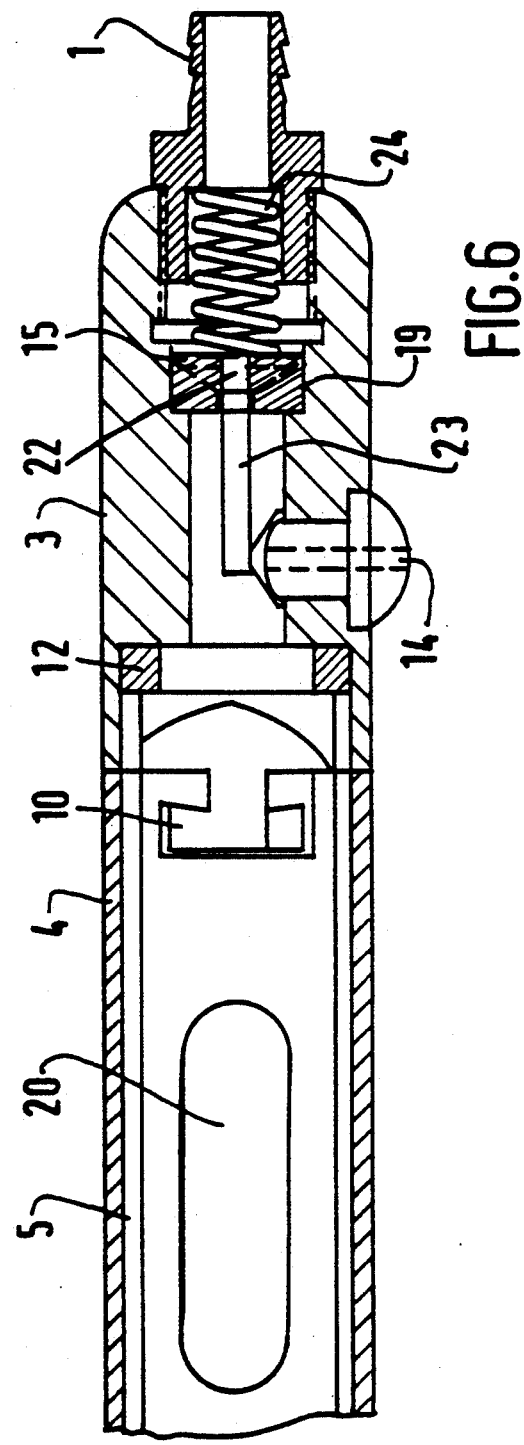

HYGIENE AND TREATMENT DEVICE

The present invention relates to a device for anal or gynecological hygiene and treatment, making it possible to perform cleaning simply, hygienically, without trauma of the organs to be treated, without using a cannula, and without making contact.

BACKGROUND OF THE INVENTION

Such hygiene and treatment measures have been recommended for a very long time, for example in the work entitled "Pathologie Interne" by Grisole, published in 1857 by Victor Masson. Such measures are intended for the treatment or the prevention of hemorroids, anal cracks and irritations, gynecological infections, and constipation.

However, until now, no simple means have been available to the public or to hospital personnel for performing this kind of washing. An object of the present invention is to mitigate this drawback.

SUMMARY OF THE INVENTION

The present invention provides a device for hygiene and treatment that comprises:
- an endpiece for connection to a supply of water under pressure;
- a stop valve;
- a chamber having a transparent wall; and
- a pipe connected at one end to the chamber and curved at its end distant from the chamber, the pipe having a linear longitudinal slot in the vicinity of the distant end.

Thus, once the pipe has been put into place, spraying can be commenced merely by opening the valve. The device can be used directly in a water closet pan, thereby providing conditions of cleanliness without requiring additional means. Water distribution pressure can thus be used directly while nevertheless being modulated by headloss.

The shape and anatomical orientation of the device ensures that external and internal portions are cleaned in such a manner as to avoid even the slightest retention of secretions and poorly-evacuated material that constitute sources of discomfort and of complications.

BRIEF DESCRIPTION OF THE DRAWINGS

Embodiments of the invention are described by way of example with reference to the accompanying drawings, in which:

FIG. 1 is an overall view of the device;

FIG. 2 is an exploded view of the transparent-walled chamber;

FIG. 3 is a section view through the top portion of the chamber;

FIG. 4 is a detail view of the top portion of the pipe;

FIG. 5 is a detail view of the bottom end of the pipe; and

FIG. 6 shows a variant embodiment of the water inlet control.

DETAILED DESCRIPTION

FIG. 1 shows a device comprising an endpiece 1 suitable for connection to a flexible hose itself connected via an appropriate coupling to a supply of water under pressure. The endpiece 1 is mounted at the top of a component 2 that may include a valve or faucet. The valve-containing component is connected to a chamber comprising two sleeve portions 3 and 4 which are removably assembled together. The bottom portion 6 of half-sleeve 4 is fixed to a pipe 7. This pipe is terminated by an end 8 which is curved, for anatomical reasons, through an angle of about 20° relative to the axis of the pipe 7. The pipe 7 is constituted by a hollow tube which is closed at its top end, i.e. its end adjacent to the chamber 3, 4, by a disk 21 which is pierced by three holes 18, as can be seen in FIG. 4. The bottom end 8 of the pipe 7 has a longitudinal slot 9 through which liquid can flow laterally, with this slot appearing in the detail view of FIG. 5. This disposition makes it possible to administer a douche in the required places by sliding the pipe 7 between the legs.

As can be seen in FIG. 2 which is an exploded view of the middle portion of the device, the device includes a transparent tube 5 inside the two-part sleeve 3, 4 whose parts are made of metal or of plastic and are generally opaque. The top and bottom ends of the transparent tube 5 bear against resilient washers 12 and 13, e.g. made of neoprene, which washers serve firstly as sealing rings for the tube 5 and secondly to provide effective locking by co-operation between a tenon 10 and a mortise 11 which constitute a bayonet fastening. According to a characteristic of the invention, the tenon 10 extending from the bottom of sleeve portion 3 is narrower than the mortise 11. As a result, when the two portions 3 and 4 of the sleeve are assembled together there remains a gap 20 constituting a vertical slot. Any other form of window could be used, e.g. an oval window as shown in FIG. 1. The purpose of the window or slot is to enable the inside of the tube 5 to be inspected visually. Medicines or antiseptics for treatment purposes or more generally any kind of medication required by the treatment can be inserted inside the chamber 5 in the form of pellets. It is necessary to be able to monitor the state of such substances, and in particular the extent to which they have been eroded by the flow of water in order to replace them when necessary, if the use of medication is itself necessary.

To prevent these substances blocking the openings 18 shown in FIG. 4, which openings serve not only to pass the water from the water supply but also to set up turbulent motion in the water, a central stud 17 is provided on the disk 21 which prevents any pellet bearing flat against the disk 21. Pellets therefore remain at an angle.

FIG. 3 is a vertical section through the top portion of the sleeve onto which the endpiece 1 is screwed directly, in this case. The endpiece 1 engages in a hose (not shown) which is in turn connected to a water supply system. A valve member 15 is to be found in a chamber formed inside the portion 3 of the sleeve and serves to close the duct 22 against the flow of water. The top portion of the valve member 15 is fixed to a flexible rod 16. Thus, by twisting the water supply hose a little, it is possible to displace the rod 16 so as to lift the valve member 15. This releases the opening 22 and allows water to flow into the device.

As shown in FIG. 6, a different solution to providing control over water feed may be provided by a pushbutton 14 disposed on the top portion of the sleeve 3 with the pushbutton engaging a rod 23. When the button 14 is pressed, the rod 23 is displaced laterally and the valve member 15 is lifted off its seat 19, thereby allowing water to flow.

The device operates as follows:

If substances are required in the tube 5, a visual check is performed to ensure that they can act effectively prior to using the pipe. If the inspection is unsatisfactory, the relevant substances are put into the chamber 5 by disassembling the sleeve 3, 4 and then closing it again. Once the pipe is in position, the valve 2 is opened either by acting on the pushbutton 14 or else by twisting the hose a little, and cleaning is performed as mentioned above.

Naturally, numerous variants may be provided, in particular by substituting technically equivalent means, without thereby going beyond the scope of the invention.

We claim:

1. A hygiene and treatment device comprising:
   a pipe having two ends with a chamber at one of its ends, suitable for connection to a supply of water under pressure, an other end of the pipe being curved to define a curved part and having a longitudinal slot in an internal wall of the curved part in a vicinity of an end surface thereof, wherein the chamber comprises two portions which are interconnected by a bayonnet fastening, a width of a male part of the bayonnet fastening being narrower than a width of a female part, thereby defining a longitudinal gap.

2. A device according to claim 1, wherein the chamber comprises a transparent tube mounted inside said two portions with the longitudinal gap and the transparent tube forming a window whereby contents of the chamber can be inspected.

3. A device according to claim 1, wherein a top end of the pipe is closed at the chamber by a disk which is pierced by holes, and further comprising a stud projecting from a center of the disk.

4. A hygiene and treatment device suitable for connection to a supply of water under pressure, comprising a chamber adjacent one end of a pipe for holding a substance, and an end part remote from the chamber that is curved through an angle relative to a longitudinal axis defined by the pipe, the end part having a longitudinal slot opening the pipe for discharge laterally through the end part, wherein the chamber comprises two portions coupled by a bayonnet fastener having a male part and a female part, the male part being narrower than the female part, thereby defining a longitudinal gap between the male part and the female part.

5. The hygiene and treatment device according to claim 4, further comprising a tube within the chamber that is transparent at the longitudinal gap, for viewing contents of the chamber.

6. The hygiene and treatment device according to claim 4, wherein the end part is curved through an angle of about 20° relative to the longitudinal axis defined by the pipe.

7. The hygiene and treatment device according to claim 4, further comprising valve means operable to adjust coupling of the chamber to the supply of water under pressure.

* * * * *